United States Patent [19]
Commereuc et al.

[11] Patent Number: 5,877,376
[45] Date of Patent: Mar. 2, 1999

[54] CONVERSION OF ETHYLENE INTO BUTENE-1 USING ADDITIVES BASED ON QUARTERNARY AMMONIUM SALTS

[75] Inventors: Dominique Commereuc, Meudon; Yves Chauvin, Le Pecq; François Hugues, Vernaison; Yves Glaize, Saint Symphorien D'Ozon, all of France

[73] Assignees: Institut Francais du Petrole, Cedex, France; Saudi Basic Industries Corporation, Riyadh, Saudi Arabia

[21] Appl. No.: 842,421

[22] Filed: Apr. 24, 1997

[30] Foreign Application Priority Data

Apr. 26, 1996 [FR] France .................................. 94 05400

[51] Int. Cl.$^6$ ...................................................... C07C 2/30
[52] U.S. Cl. ............................ 585/513; 585/512; 585/524
[58] Field of Search ..................................... 585/513, 512, 585/524

[56] References Cited

U.S. PATENT DOCUMENTS

| | | | |
|---|---|---|---|
| 4,532,370 | 7/1985 | LéQuan et al. | 585/512 |
| 4,615,998 | 10/1986 | LéQuan et al. | 502/126 |

*Primary Examiner*—Bekir L. Yildirim
*Attorney, Agent, or Firm*—Millen, White, Zelano, & Branigan, P.C.

[57] ABSTRACT

The invention concerns an improved process for the conversion of ethylene into butene-1, wherein the ethylene is brought into contact with a catalyst obtained by the reaction of an alkyl titanate, possibly mixed with an ether, with a compound of aluminium of the formula $AlR_3$ or $AlR_2H$, and in the presence of an additive formed by at least one quaternary ammonium salt.

19 Claims, No Drawings

CONVERSION OF ETHYLENE INTO BUTENE-1 USING ADDITIVES BASED ON QUARTERNARY AMMONIUM SALTS

FIELD OF THE INVENTION

The present invention concerns an improved process for the synthesis of butene-1 by the dimerisation of ethylene, by virtue of the use of additives based on quaternary ammonium salts.

BACKGROUND OF THE INVENTION

In the process for the dimerisation of ethylene to give but-1-ene by means of a homogeneous catalyst obtained by the interaction of a preformed mixture of an alkyl titanate and an ether with a compound of aluminium of the formula $AlR_3$ or $AlR_2H$ as described in U.S. Pat. Nos. 4,532,370 and 4,615,998, small amounts of solid polymer are formed, which are deposited on the surface of the reactor and the heat exchanger tubes and which are very harmful to good operation of the process as they reduce the rate of heat transfer effects and necessitate frequent derivatives of the reactor in order for them to be removed.

SUMMARY OF THE INVENTION

It has now been found that, if the dimerisation reaction is conducted in the presence of additives formed by quaternary ammonium salts, the amount of solid by-product polymer is reduced and the adhesion thereof to the walls of the reactor and the exchangers is considerably reduced.

The invention thus concerns an improved process for the conversion of ethylene into butene, wherein, in a reaction enclosure, the ethylene is brought into contact with a solution of a catalyst obtained by the reaction of at least one alkyl titanate with a compound of aluminium of the formula $AlR_3$ or $AlR_2H$, each of the residues R being a hydrocarbyl radical, and in the presence of at least one additive selected from the group formed by quaternary ammonium salts.

The elements of the catalyst solution are described in U.S. Pat. Nos. 4,532,370 and 4,615,998, the teachings of which are included herein.

The alkyl titanates used in the invention correspond to the general formula $Ti(OR')_4$ in which R' is a branched or straight chain alkyl radical comprising preferably from 2 to 8 carbon atoms. The following may be mentioned by way of example: tetraethyl titanate, tetraisopropyl titanate, tetra-n-butyl titanate and 2-tetraethylhexyl titanate.

In a particularly advantageous embodiment the catalyst solution results from the reaction of a preformed mixture of at least one alkyl titanate and at least one ether, with at least one aluminium compound as defined above. It has been found that the addition of ether makes it possible to reduce the amount of polymer formed upon conversion. The ethers which can be used may be monoethers or polyethers. It is possible for example to use diethylether, diisopropylether, dibutylether, methyl-t-butylether, tetrahydrofuran, 1,4-dioxan, dihydropyran and ethyleneglycoldimethylether. The preferred ethers are tetrahydrofuran and/or 1,4-dioxan. They are used alone or in the form of a mixture.

The ethers are used in a molar ratio of from 0 to 10, advantageously from 0.1 to 10 or from 0.5 to 10, preferably from 1 to 5, more particularly from 2 to 4 moles of etherper mole of compound of titanium. Without being bound to any theory, it can be thought that the ether complexes itself on to the titanium, thus permitting it to be hexacoordinated. If the ether is used in ratios of higher than 10 moles of ether per mole of titanium, for example 20 and above, or if it is used as a solvent for the reaction, it is observed that the reaction is considerably slowed down and that its selectivity is less good and even in some cases the reaction no longer takes place at all.

The compounds of aluminium which are used to prepare the catalyst are represented by the general formula $AlR_3$ or $AlR_2H$ in which R is a hydrocarbyl radical, preferably alkyl, comprising from 2 to 6 carbon atoms. The compound $AlR_3$ is preferred. Triethylaluminium, tripropylaluminium, tri-iso-butylaluminium and trihexylaluminium may be mentioned by way of example.

The components of the catalyst may be brought into contact in a hydrocarbon and/or in particular in the butene-1 produced by dimerisation and/or in the by-products of the dimerisation reaction such as hexenes, preferably in the presence of ethylene. The molar ratio between the compound of aluminium and that of titanium is about 1:1 to 20:1 and preferably about 2:1 to 5:1. The concentration of titanium in the solution prepared in that way is advantageously between $10^{-4}$ and 0.5 mole per liter and preferably between $2.10^{-3}$ and 0.1 mole per liter.

The temperature at which preparation of the catalyst is effected is usually between $-10°$ and $+80°$ C., preferably between $-10°$ and $+45°$ C. When ethylene is present in the medium, the amount thereof preferably corresponds to saturation of the solution at the operating temperature at pressure, 1 bar or more. The catalyst solution obtained in that way can be used as it is or it can be diluted by the addition of the products of the reaction.

The quaternary ammonium salts which are used in accordance with the invention correspond to the general formula $[(R_1R_2R_3R_4)N^+]X^-$ in which $R_1$, $R_2$, $R_3$ and $R_4$ are identical or different hydrocarbyl radicals, for example alkyl, cycloalkyl, aryl, cycloalkyl or aryl which are substituted by an alkyl group, comprising from 1 to 30 carbon atoms, and X is a monovalent anion, for example a halide or a hydroxide. The following may be mentioned by way of example: tetraethylammonium chloride, tetraethylammonium bromide, trimethyl-cetylammonium chloride, trimethyl-cetylammonium bromide, dimethyl-dilaurylammonium chloride, methyl-trioctylammonium chloride, methyl-tridecylammonium chloride and benzyl-dimethyl-cetylammonium chloride. The bromides are the preferred salts. The quaternary ammonium salts may be used as they are or in the form of a solution in a hydrocarbon medium selected from the group formed by hydrocarbons and/or the dimerisation product but-1-ene and/or by a or the by-products of the reaction such as hexenes.

Whether it is a continuous or discontinuous process the quaternary ammonium salts, pure or in solution, may be introduced before proceeding with the ethylene dimerisation reaction, for example they may be used to effect a treatment for passivation of the walls of the reaction enclosure prior to the reaction being started. The walls of the enclosure are metallic (metals, steels, alloys . . . ) and may have been subjected to protective treatments (polishing, vitrification . . . ) or may have been subjected to anodic protection.

Passivation is effected using any of the known procedures. Advantageously the enclosure is charged with a solution of 20 ppm to 5% by weight of additive in a hydrocarbon medium, contact is maintained preferably with agitation for from 10 minutes to 10 hours, preferably from 30 minutes to 3 hours, and at a temperature below the boiling temperature of the solvent, from $20°$ to $100°$ C. generally and from $30°$ to $80°$ C. preferably. The solution is then generally discharged.

The quaternary ammonium salts, pure or in solution, can also be introduced continuously or discontinuously while the reaction is taking place, for example in the form of a mixture with the solution of the titanate, preferably in the form of a flow which is independent of the catalyst flows. It may be advantageous to combine a preliminary treatment for passivation of the reaction enclosure, followed by continuous or discontinuous injection while the reaction is taking place.

The amount of quaternary ammonium salts used during the dimerisation reaction may represent from 1 part per million by weight (ppm) to 5% by weight, advantageously 1 ppm to 1%, preferably 20 ppm to 5000 ppm, with respect to the butene-1 produced, whether that amount is introduced during the reaction (continuous process) or into the enclosure prior to the reaction (discontinuous process).

The ethylene dimerisation reaction can be performed at a temperature of from 20° to 150° C., preferably from 20° to 70° C. and still more preferably from 40° to 70° C. The pressure is preferably from 0.5 to 8 MPa.

In a mode of performing the catalytic dimerisation reaction discontinuously, the procedure involves introducing into the reactor (reaction enclosure) which is provided with the usual agitation and cooling systems, the additive with the catalyst solution, for example a selected volume of catalytic solution, prepared as described above, and, independently, a selected volume of a solution of quaternary ammonium salt, after which it is pressurised by means of ethylene and the temperature is adjusted to the desired value. The reactor is fed with ethylene at a constant pressure until the total volume of liquid produced almost completely fills the reactor. The catalyst is destroyed after reaction, for example by the injection of water, ammonia or an amine, and the products of the reaction and the solvents if used are drawn off and separated.

In the case of continuous operation it is advantageously possible to begin each procedure by passivation of the walls of the reactor with a selected volume of a solution of quaternary ammonium salt. After that solution has been drawn off and the reactor advantageously rinsed with a hydrocarbon, the catalytic solution is injected continuously at the same time as a quaternary ammonium salt solution and at the same time as the ethylene. The temperature and pressure are kept constant by means of any usual regulating system. The effluent from the reactor is passed into a system of distillation columns which permits separation on the one hand of the butene-1 from the ethylene, which is returned to the reactor, and on the other hand the hexenes and the octenes which are by-products of the reaction and of which a part can be passed into the catalyst preparation section. The column bottom containing the catalyst, the heavy by-products and the additive can be incinerated or else the recovered catalyst is recycled.

The following Examples illustrate the invention without limiting the scope thereof.

EXAMPLE 1 to 4

A series of tests was carried out to determine the inhibiting effect of the quaternary ammonium salts on the formation and adhesion to the walls of the polymer which is a by-product in the dimerisation of ethylene to form butene-1. The effect of the production of polymer is very substantial in terms of fouling of the walls of the reactor and the tubes of the exchangers because it limits the rate of heat transfer, thereby lowering the rate of removal of the reaction heats. This harmful effect is observed even when the amount of ethylene transformed into polymer is very low in relation to the amount of ethylene which is dimerised to give butene-1.

The ethylene dimerisation reaction is effected using an autoclave of Grignard type of stainless steel, of a volume of 250 ml provided with a double jacket permitting regulation of the temperature by a circulation of water, and a magnetic stirrer rod.

In each example the catalyst is prepared at a temperature of 25° C. by successively introducing the following into the reactor under an atmospheric pressure of ethylene: 25 ml of heptane, 9.8 ml of a solution of 0.5 ml of triethylaluminium in 19.5 ml of heptane (that is to say 1.77 mmole), 2 ml of a 10% solution by volume of tetra-n-butyltitanate in heptane (that is to say 0.59 mmole) and an amount of the additive quaternary ammonium salt which is variable according to the tests. After 2 minutes of reaction the temperature is raised to 70° C. and the ethylene pressure to 2 MPa.

The dimerisation reaction is stopped by the injection of 2 ml of water when about 100 gaseous liters (related to normal conditions) of ethylene have been consumed. The reactor is then depressurised, the gas being recorded in the operating procedure account and collected in a gasometer to be analysed. After the reactor has been opened, the liquid and solid content thereof is collected and washed with 20 ml of a 10% sulphuric aqueous solution in order to redissolve the catalyst residues. The remaining solid polymer is filtered, dried for one night in a drying oven at 110° C. and weighed.

The results of the test are set out in Table 1 which shows for each test: the nature of the additive, the amount of additive used expressed in parts per million by weight (ppm) with respect to the butene-1 formed, the activity of the catalyst expressed by the number of moles of ethylene consumed per hour, the amount of polymer formed in ppm with respect to the ethylene transformed, and the physical appearance of the polymer.

Example 1 is a comparative Example in the absence of additive which is not part of the invention. In comparison it is clear that the use of an additive formed by a quaternary ammonium salt has a totally beneficial effect on the amount of polymer formed on the one hand, which is greatly reduced, and its adhesion to the walls on the other hand, which is much less, thus facilitating the removal thereof.

TABLE 1

| No Additive | Additive/ butene-1 (ppm) | Activity (mole $C_2$/h) | Polymer (ppm) | Appearance |
|---|---|---|---|---|
| 1 without | 0 | 6.0 | 2330 | (a) |
| 2 $(C_2H_5)_4N^+Cl^-$ | 330 | 4.1 | 1450 | (b) |
| 3 $(C_2H_5)_4N$ Br | 400 | 4.2 | 430 | (b) |
| 4 $[(CH_3)_3(C_{16}H_{33})]N$ Br | 850 | 4.0 | 230 | (b) |

(a) polymer which clings very firmly to the walls
(b) polymer in granule form with a very low level of adhesion

We claim:

1. In a process for the conversion of ethylene to butene-1, wherein, in a reaction enclosure, the ethylene is brought into contact with a solution of a catalyst resulting from the reaction of at least one alkyl titanate with at least one aluminum compound of the formula $AlR_3$ or $AlR_2H$, each of the residues R being a hydrocarbyl radical, the improvement comprising conducting the conversion reaction in the presence of at least one quaternary ammonium salt.

2. A process according to claim 1 wherein the catalyst solution results from the reaction of a preformed mixture of at least one alkyl titanate and at least one ether, with at least one aluminium compound of the formula $AlR_3$ or $AlR_2H$, each of the residues R being a hydrocarbyl radical.

3. A process according to claim 1 wherein the concentration of titanium in the catalyst solution is between $10^{-4}$ and 0.5 mole per liter.

4. A process according to claim 1 wherein the molar ratio between the aluminium compound and the titanium compound is between 1:1 and 20:1.

5. A process according to claim 2 wherein the molar ratio between the ether and the titanium compound is less than or equal to 10.

6. A process according to claim 1 wherein the aluminium compound is $AlR_3$.

7. A process according to claim 1 wherein the quaternary ammonium salt is a quaternary ammonium hydroxide or halide.

8. A process according to claim 1 wherein the additive is a quaternary ammonium bromide.

9. A process according to claim 1 wherein the quaternary ammonium salt comprises identical or different hydrocarbyl radicals comprising from 1 to 30 carbon atoms.

10. A process according to claim 1 wherein the additive is used in the form of a solution in a hydrocarbon medium selected from the group consisting of hydrocarbons, a dimerisation product, the reaction by-product or by-products and mixtures thereof.

11. A process according to claim 1 wherein the additive is used in the pure state.

12. A process according to claim 1 wherein, before proceeding with the conversion reaction, the additive is introduced into the reaction enclosure to effect a treatment for passivation of the walls of the enclosure.

13. A process according to claim 1 wherein the additive is introduced while the conversion reaction is taking place, the process being continuous.

14. A process according to claim 1 wherein, the process being discontinuous, the additive is introduced into the reaction enclosure with the catalyst solution.

15. A process according to claim 1 wherein the additive is introduced independently of the catalyst solution.

16. A process according to claim 1 wherein the amount of quaternary ammonium salt used during the conversion reaction is from 1 ppm to 5% by weight with respect to the butene-1 produced.

17. A process according to claim 1 wherein the amount of quaternary ammonium salt used during the conversion reaction is from 20 ppm to 5000 ppm with respect to the butene-1 produced.

18. A process according to claim 1 wherein the conversion reaction takes place at a temperature of between 20° and 150° C. under a pressure of from 0.5 to 8 MPa.

19. A process according to claim 1 wherein the additive is selected from the group consisting of tetraethylammonium chloride, tetraethylammonium bromide, trimethyl-cetylammonium chloride, trimethyl-cetylammonium bromide, dimethyl-dilaurylammonium chloride, methyl-trioctylammonium chloride, methyl-tridecylammonium chloride and benzyl-dimethyl-cetylammonium chloride.

* * * * *